United States Patent [19]

Rapp et al.

[11] 4,031,139
[45] June 21, 1977

[54] MANUFACTURE OF CYCLOHEXANONE OXIME

[75] Inventors: Guenther Rapp; Hugo Fuchs, both of Ludwigshafen; Erwin Thomas, Freinsheim, all of Germany

[73] Assignee: BASF Aktiengesellschaft, Ludwigshafen (Rhine), Germany

[22] Filed: Jan. 26, 1976

[21] Appl. No.: 652,421

[30] Foreign Application Priority Data

Feb. 26, 1975 Germany .......................... 2508247

[52] U.S. Cl. .......................................... 260/566 A
[51] Int. Cl.$^2$ ...................................... C07C 131/04
[58] Field of Search .............................. 260/566 A

[56] References Cited

UNITED STATES PATENTS

| 3,429,920 | 2/1969 | De Rooij ...................... 260/566 A |
| 3,729,304 | 4/1973 | Elmendorp et al. ........... 260/566 A |
| 3,862,230 | 1/1975 | De Rooij et al. .............. 260/566 A |

FOREIGN PATENTS OR APPLICATIONS 1,138,750  1/1969  United Kingdom .......... 260/566 A

*Primary Examiner*—Gerald A. Schwartz
*Attorney, Agent, or Firm*—Johnston, Keil, Thompson & Shurtleff

[57] ABSTRACT

An improved process for the manufacture of cyclohexanone oxime by reacting cyclohexanone with an aqueous hydroxylammonium-ammonium sulfate solution at temperatures above the melting point of cyclohexanone oxime by the countercurrent process, the improvement consisting in that the reaction is carried out in the absence of solvents and neutralizing and/or buffer salts at pHs of up to 0.5 until equilibrium is reached, the oximes resulting during the reaction being separated from the aqueous phase and the aqueous phase being extracted with cyclohexanone and then subjected to steam distillation.

2 Claims, No Drawings

MANUFACTURE OF CYCLOHEXANONE OXIME

Cyclohexanone oxime is used in the manufacture of caprolactam.

It is known to manufacture cyclohexanone oxime by reacting cyclohexanone with an aqueous solution of hydroxylammonium sulfate with addition of ammonia to neutralize the sulfuric acid liberated during the reaction. Thus ammonium sulfate is formed as a byproduct in an amount depending on the method of manufacture of the hydroxylamine, and which ranges from 0.7 to 2.7 parts of ammonium sulfate per part of cyclohexanone oxime formed.

To reduce the amount of ammonium sulfate produced, a number of patent applications propose that oximation be carried out in buffer systems at low pHs or that the ammonium sulfate formed be decomposed thermally to ammonium bisulfate and the latter reused in the catalytic synthesis of hydroxylamine in place of sulfuric acid. The aqueous acid solutions produced after oximation are recycled to the hydroxylamine synthesis. For example, German Printed Application 1,271,711 describes the manufacture of cyclohexanone oxime by reaction of cyclohexanone with an aqueous hydroxylammonium sulfate solution in the first stage at elevated temperatures and in the presence of an ammonium sulfate/ammonium bisulfate buffer solution at pHs of from 1.5 to 3. The oxime is then reacted in a second stage with excess hydroxylamine at pHs greater than 3.

German Laid-Open Applications 1,493,198 and 2,046,256 describe for instance the preparation of cyclohexanone oxime in the presence of soluble salts of weak acids serving as buffer system during the formation of the oxime, and German Laid-Open Application 2,129,658 describes oxime synthesis by means of hydroxylammonium sulfate in the presence of ammonium bisulfate and ammonium biphosphate at pHs of at least 0.5. Finally, German Printed Application 1,272,288 describes the manufacture of oxime by the countercurrent method using low pHs in a buffered acid system and in the presence of solvents which are inert to the oximation reaction and are immiscible or only slightly miscible with water.

All of the said processes aim at reducing or obviating the formation of ammonium sulfate as by-product in the manufacture of cyclohexanone oxime and the reuse of the acid aqueous solution which is formed during oximation for the synthesis of hydroxylamine. The said processes, generally speaking, operate in the presence of neutralizing salts such as ammonium nitrate or in the presence of buffer systems such as ammonium sulfate/ammonium bisulfate or phosphoric acid/ammonium dihydrogen phosphate, or oximation is additionally carried out in the presence of solvents which are immiscible or only slightly miscible with water.

This involves relatively expensive solvent regeneration and the circulation of a high concentration of ballast salt, the latter having a detrimental effect of the conversion of NO and the yield of hydroxylamine in the synthesis of hydroxylamine by NO hydrogenation associated with said oximation. The said processes also usually require post-oximations in a second stage at higher pHs in order to obtain complete conversion of the cyclohexanone used.

We have now found that these drawbacks occurring in the manufacture, by the countercurrent method, of cyclohexanone oxime by conversion of cyclohexanone with an aqueous hydroxylammonium/ammonium sulfate solution at temperatures above the melting point of cyclohexanone oxime may be avoided if the reaction is carried out in the absence of solvents and neutralizing and/or buffering salts at pHs of up to 0.5 equilibrium is reached, the oxime formed is separated from the aqueous phase and the aqueous phase is extracted with cyclohexanone and then subjected to steam distillation.

Conversions achieved may range up to more than 90%, based on the cyclohexanone introduced, and the cyclohexanone oxime formed contains not more than 2% of cyclohexanone and may be used directly to give caprolactam by catalytic gas-phase rearrangement. The resulting aqueous phase may also be used advantageously, without additional salt ballast, in place of sulfuric acid in the synthesis of hydroxylamine by catalytic reduction of nitrogen monoxide with hydrogen.

An advantageous embodiment of our process is described below. The starting solution is an aqueous solution of hydroxylammonium/ ammonium sulfate such as is obtained in the catalytic reduction of nitrogen monoxide with hydrogen in contact with noble metal catalysts in a solution of ammonium bisulfate. This solution is caused to react with cyclohexanone without the addition of neutralizing salts such as ammonium nitrate, or buffering salts such as ammonium sulfate/ammonium bisulfate or phosphoric acid/ammonium dihydrogen phosphate. The reaction is advantageously carried out by the countercurrent method in a column, for example a rotating disk column or pulsed packed column, or in stirred containers connected to form a cascade. In the one case the cyclohexanone is reacted in excess with the hydroxylammonium/ammonium sulfate solution, and in the other case the hydroxylamine solution is reacted in excess with cyclohexanone. The overall ratio of cyclohexanone to hydroxylamine should be stoichiometric. The reaction is carried out at a temperature which is above the melting point of the cyclohexanone formed during the reaction. The pH of the aqueous phase formed during the reaction is 0.5 or less at the reaction temperature. If the reaction is carried out in a column, the organic phase consisting of the product cyclohexanone oxime containing a small amount of water and unreacted cyclohexanone separates at the top of the column. The aqueous phase collecting at the bottom of the column contains ammonium bisulfate, a small amount of hydroxylamine, some dissolved oxime and cyclohexanone.

This aqueous phase is then extracted with the fresh cyclohexanone required for the reaction, and the organic phase separating after the extraction and consisting of cyclohexanone and the oxime absorbed during extraction is passed to the oximation zone. The aqueous phase is then subjected to azeotropic distillation in order to remove and recover dissolved cyclohexanone. The cyclohexanone separating from the distillate as the light phase may be combined with fresh cyclohexanone for use in the oximation process.

The aqueous ammonium bisulfate phase freed from organic products such as cyclohexanone oxime and cyclohexanone may be used directly or, for example, after treatment with carbon for the removal of the final traces of organic components, in the catalytic hydroxylamine synthesis in place of sulfuric acid. Here again there is produced a hydroxylammonium/ammonium sulfate solution which may then be used for the oximation process. The aqueous ammonium bisulfate solution formed during oximation may, of course, be passed to the hydroxylamine synthesis as formed or, if desired, in a diluted or concentrated form. The oxime phase produced by the oximation reaction may be used directly, without post-oximation or purification, to particular advantage for catalytic rearrangement to caprolactam in the gas phase, the catalyst being, say, boron oxide/aluminum oxide.

Alternatively, the oxime may be post-oximated at higher pHs and rearranged to caprolactam by conventional methods.

The process of the invention is distinguished from prior art processes for the manufacture of cyclohexanone oxime in that it is carried out in the absence of organic solvents and in the absence of neutralizing and/or buffering salts at pHs of less than 0.5. The degree of conversion, based on cyclohexanone introduced, is greater than 90%. Thus no expensive solvent regeneration is required and no salt ballast is circulated which could be detrimental to the catalytic hydroxylamine synthesis. There is no reduction in the NO conversion and hydroxylamine yield compared with conventional NO hydrogenation in sulfuric acid.

In spite of the presence of small amounts of unreacted cyclohexanone in the oxime formed, the latter can be directly used for catalytic gas phase rearrangement to caprolactam.

EXAMPLE 12.235 kg of a hydroxylammonium/ammonium sulfate solution of the following composition is fed, per hour, to the top end of a pulsed glass column packed with Raschig rings:

7.463 kg of $H_2O$
4.295 kg of $(NH_3OH-NH_4)SO_4$
0.355 kg of $NH_4HSO_4$
0.122 kg of $(NH_4)_2SO_4$.

To the bottom end there are fed 3.292 kg/hr of a mixture of cyclohexanone and cyclohexanone oxime having a cyclohexanone content of 2.854 kg. The reaction temperature is 90° C. 3.067 kg/hr of cyclohexanone oxime having a cyclohexanone content of 0.6% and a water content of 4.6% is drawn off at the top of the column. The cyclohexanone oxime obtained may be directly used for catalytic gas phase rearrangement to caprolactam.

The aqueous phase obtained at the bottom of the column at a rate of 12.46 kg/hr has a pH of about 0.3 at 25° C and has the following composition:

7.806 kg of water
0.145 kg of cyclohexanone
0.637 kg of cyclohexanone oxime
3.457 kg of $NH_4HSO_4$
0.122 kg of $(NH_4)_2SO_4$
0.293 kg of $(NH_3OH-NH_4)SO_4$.

To remove dissolved cyclohexanone oxime, the solution is extracted countercurrently with 2.536 kg of fresh cyclohexanone and 0.318 kg of recycled cyclohexanone. There is thus produced 3.292 kg of a cyclohexanone/cyclohexanone oxime mixture as the lighter phase, this being reused in the oximation. The aqueous phase contains even smaller amounts of oxime and dissolved cyclohexanone. From this aqueous phase 0.318 kg of cyclohexanone can be recovered by azeotropic distillation; this recovered material is recycled together with fresh cyclohexanone.

The recovered cyclohexanone is composed of the cyclohexanone obtained by azeotropic distillation and the cyclohexanone obtained under the distillation conditions at low pHs by redissociation of the remaining cyclohexanone oxime. After removal of the cyclohexanone, the aqueous distillate phase is recycled to the column.

To improve the purity of this aqueous phase, it may be subjected to a carbon treatment at 40° C.

The amount of aqueous phase obtained is 11.704 kg and it has the following composition:

7.774 kg of $H_2O$
3.255 kg of $NH_4HSO_4$
0.553 kg of $(NH_3OH-NH_4)SO_4$
0.122 kg of $(NH_4)_2SO_4$
carbon content about 0.02%.

This solution is then treated with a 2:1 v/v mixture of hydrogen and nitrogen monoxide in the presence of a platinum catalyst and with rapid stirring. The resulting hydroxylammonium/ammonium sulfate solution may be returned to the oximation cycle. The degree of conversion is from 0.3 to 0.5 mole of nitrogen monoxide per liter of reaction space per hour. Small amounts of ammonium sulfate formed may be decomposed by known methods, for example by treatment with nitric oxides.

We claim:

1. An improved process for the manufacture of cyclohexanone oxime by reaction of cyclohexanone with an aqueous hydroxylammonium/ammonium sulfate solution at temperatures above the melting point of cyclohexanone oxime by the countercurrent method, the improvement comprising: carrying out the reaction in the absence of solvents and neutralizing and/or buffering salts at pHs of 0.5 or less until a state of equilibrium is reached, removing the oxime produced during the reaction from the aqueous phase and extracting the aqueous phase with cyclohexanone and then subjecting the extracted aqueous phase to steam distillation.

2. A process as claimed in claim 1, wherein the aqueous phase is used in place of sulfuric acid in the synthesis of hydroxylamine by catalytic reduction of nitrogen monoxide with hydrogen in contact with noble metal catalysts.

* * * * *